US010653898B2

(12) United States Patent
Soroudi

(10) Patent No.: US 10,653,898 B2
(45) Date of Patent: May 19, 2020

(54) NON-IRRITATING, NON-BLURRING OPHTHALMIC SUNSCREEN

(71) Applicant: A. Ebbie Soroudi, M.D., M.S., A Professional Medical Corporation, Los Angeles, CA (US)

(72) Inventor: A. Ebbie Soroudi, Los Angeles, CA (US)

(73) Assignee: A. EBBIE SOROUDI, M.D., M.S., A PROFESSIONAL MEDICAL CORPORATION, Los Angeles, CA (US)

( * ) Notice: Subject to any disclaimer, the term of this patent is extended or adjusted under 35 U.S.C. 154(b) by 0 days.

(21) Appl. No.: 16/540,962

(22) Filed: Aug. 14, 2019

(65) Prior Publication Data

US 2020/0069977 A1    Mar. 5, 2020

Related U.S. Application Data

(62) Division of application No. 14/715,894, filed on May 19, 2015, now Pat. No. 10,420,963.

(60) Provisional application No. 62/000,071, filed on May 19, 2014.

(51) Int. Cl.

| | | |
|---|---|---|
| *A61Q 17/04* | (2006.01) | |
| *A61K 8/02* | (2006.01) | |
| *A61K 8/06* | (2006.01) | |
| *A61Q 19/00* | (2006.01) | |
| *A61K 8/46* | (2006.01) | |
| *A61K 8/37* | (2006.01) | |
| *A61K 8/29* | (2006.01) | |
| *A61K 8/27* | (2006.01) | |

(52) U.S. Cl.
CPC ............ *A61Q 17/04* (2013.01); *A61K 8/0241* (2013.01); *A61K 8/06* (2013.01); *A61K 8/27* (2013.01); *A61K 8/29* (2013.01); *A61K 8/37* (2013.01); *A61K 8/466* (2013.01); *A61Q 19/00* (2013.01); *A61K 2800/26* (2013.01); *A61K 2800/412* (2013.01)

(58) Field of Classification Search
None
See application file for complete search history.

(56) References Cited

U.S. PATENT DOCUMENTS

| | | |
|---|---|---|
| 4,603,046 A | 7/1986 | Georgalas et al. |
| 4,765,977 A | 8/1988 | Baron |
| 4,788,007 A | 11/1988 | Baron |
| 4,923,693 A | 5/1990 | Michalos |
| 5,041,224 A | 8/1991 | Ohyama et al. |
| 5,041,244 A | 8/1991 | Baron |
| 5,552,135 A | 9/1996 | Cioca et al. |
| 7,910,090 B2 | 3/2011 | Dueva-Koganov et al. |
| 10,420,963 B2 | 9/2019 | Soroudi |
| 2007/0092457 A1 | 4/2007 | Librizzi et al. |
| 2007/0092458 A1 | 4/2007 | Librizzi et al. |
| 2007/0218021 A1 | 9/2007 | Wells |
| 2009/0068255 A1 | 3/2009 | Yu et al. |
| 2009/0087394 A1 | 4/2009 | Beasley et al. |
| 2009/0098070 A1 | 4/2009 | Karpov et al. |
| 2010/0196291 A1 | 8/2010 | Halimi et al. |
| 2010/0226867 A1 | 9/2010 | Dueva-Koganov et al. |
| 2011/0086075 A1 | 4/2011 | Halimi et al. |
| 2011/0250153 A1 | 10/2011 | Owen et al. |
| 2012/0107253 A1 | 5/2012 | Xing et al. |
| 2012/0213842 A1 | 8/2012 | Birbara et al. |
| 2013/0028853 A1 | 1/2013 | Nurse et al. |
| 2013/0266525 A1 | 10/2013 | Piconi et al. |
| 2013/0331362 A1 | 12/2013 | Smith |
| 2015/0272848 A1 | 10/2015 | Holyfield |
| 2015/0328148 A1 | 11/2015 | Smith et al. |
| 2016/0008237 A1 | 1/2016 | Goldstein et al. |

OTHER PUBLICATIONS

"Final Office action dated Aug. 10, 2018 for U.S. Appl. No. 14/715,894.".
PCT/US2017/041784 International Search and Written Opinion dated Sep. 8, 2017.
U.S. Appl. No. 14/715,894 Notice of Allowance dated Jun. 28, 2019.
U.S. Appl. No. 14/715,894 Office Action dated Dec. 15, 2016.
U.S. Appl. No. 14/715,894 Office Action dated Jun. 21, 2017.
U.S. Appl. No. 14/715,894 Office Action dated Jun. 3, 2019.
U.S. Appl. No. 14/715,894 Office Action dated Nov. 2, 2017.
U.S. Appl. No. 15/648,107 Office Action dated Aug. 28, 2019.
U.S. Appl. No. 15/648,107 Office Action dated Jan. 3, 2019.
U.S. Appl. No. 15/648,107 Office Action dated May 7, 2018.

*Primary Examiner* — David J Blanchard
*Assistant Examiner* — Sarah J Chickos
(74) *Attorney, Agent, or Firm* — Wilson Sonsini Goodrich & Rosati

(57) ABSTRACT

A non-irritation, non-blurring ophthalmic sunscreen composition contains a liquid vehicle base, such as an artificial tear formulation or an ophthalmic suspension or ointment. The composition includes at least one inorganic and/or at least one organic active ingredient. The inorganic active ingredients may include, but not be limited to zinc oxide, titanium dioxide, iron oxide, zirconium oxide, and cerium oxide. The organic active ingredients may include, but not be limited to dioxybenzone, octinoxate, octisalate, homosalate, avobenzone, octocrylene, para-aminobenzoic acid, cinoxate, methyl anthranilate, octocrylene, padimate O, ensulizole, sulisobenzone, trolamine salicylate, and ecamsule.

8 Claims, No Drawings

NON-IRRITATING, NON-BLURRING OPHTHALMIC SUNSCREEN

CROSS-REFERENCE TO RELATED APPLICATIONS

This application is a divisional application of U.S. patent application Ser. No. 14/715,894, filed on May 19, 2015, which claims priority to provisional application 62/000,071 filed on May 19, 2014, each of which are hereby incorporated by reference.

DESCRIPTION

Field of the Invention

The present invention generally relates to a sunscreen formulation designed for protecting the eyes including the conjunctiva, cornea, lens, and retina. More particularly, the present invention relates to a non-irritating sunscreen that is applied directly onto the ocular surface of the eye for protection from ultraviolet radiation.

Background of the Invention

Ultraviolet radiation is part of the electromagnetic spectrum that reaches the earth from the sun. It has wavelengths shorter than visible light, making it invisible to the naked eye. These wavelengths are classified as UVA, UVB, or UVC. UVA has the longest of the three at 320-400 nanometers. UVA is further divided into two wave ranges, UVA I, which measures 340-400 nanometers (nm, or billionths of a meter), and UVA II which extends from 320-340 nanometers. UVB ranges from 290 to 320 nm. With even shorter rays, most UVC is fortunately absorbed by the ozone layer and does not reach the earth.

Both UVA and UVB penetrate the Earth's atmosphere and play an important role in conditions such as premature skin aging, eye damage, hair damage, and certain skin cancers.

Photoconjunctivitis and Photokeratitis describe conditions where ultraviolet radiation inflames and/or damages the delicate structures of the ocular surface (the conjunctiva and the cornea, respectively). UV exposure to the eyes (either direct or indirect) can cause severe redness, dryness, irritation, tearing, photosensitivity, and pain. This pain can be so severe as to cause chemosis and sloughing of the corneal epithelium with resultant scarring and even permanent vision loss.

Long-term ophthalmic exposure to UV radiation has been associated with permanent thickening of the conjunctiva (called a pingueculum), vascular proliferation and tissue growth over the cornea (called a pterygium), conjunctival discoloration (melanosis), even cancer (e.g., conjunctival/uveal melanoma).

Long-standing UV exposure to the eyes has also been associated with damage to the internal structures of the eyes, e.g., the natural lens and the retina. Certain forms of cataracts (e.g., nuclear sclerosis), as well as macular degeneration have been linked to the damage caused by oxidative damage from UV exposure.

Accordingly, protecting the ocular structures form UV radiation may be beneficial in preventing such oxidative damage that leads to all of these very common ophthalmic conditions. Until recently, the only proposed mechanism to protect the eyes from UV radiation has been the use of glasses with UV protection, sunglasses, and tinted contact lenses.

There is a plethora of prior art suggesting the use of different physical and/or chemical sunscreen compositions for just that skin and formulations that don't damage the eye should any formulation get within the eye, but these patents and prior art did not envision and/or describe the use of such formulations for protecting the ocular structures in any way. For example, Dueva-Koganov et al. (Pub. No.: US 2010/0226867 A1) proposed a "cosmetic and/or dermatological" composition that are non-irritating to mammalian eyes. While this is a significant advantage for a dermatological composition not to burn the eyes in case of inadvertent contact, it does not describe the application of a solution that is designed for "ophthalmic" use per se.

There have been inventions that have proposed formulations specifically for the purpose of protecting the human eye from UV radiation, but such prior art has suggested formulations that are very different than what is proposed herein with potential side-effects that may render them impractical for frequent use. Such prior art has proposed compositions that would make vision extremely blurry and/or be extremely irritating to the eyes, thus making them less suitable for frequent use by the general population.

For example Michalos (U.S. Pat. No. 4,923,693) proposed the use of 0.3-0.4% hydroxypropylmethylcellulose in the form of an eyedrop or ointment applied to the eyes prior to exposure to UV radiation). This formulation, while effective against UV radiation, would affect vision tremendously and make it difficult for the user to see clearly for hours.

Baron (U.S. Pat. No. 5,041,244) described an ophthalmic liquid sunglass that is composed of dosages of chromophores in aqueous gel to block transmission of all or various spectrums of UV from the eyes. He has described the use of high molecular weight polymers which form viscous dispersions and can be used to prolong the curation of the chromophore when the gel is applied to the eye. This alone would cause significant blurring of the users' vision. Further, there is no mention of the irritation that's caused once this mixture is directly applied to the eye. This makes Baron's invention not entirely practical for frequent use by the public.

This present disclosure describes the composition of a sunscreen solution, suspension, emulsion, and/or an ointment that is designed to be directly applied to the eye itself to protect it from UV damage without causing significant irritation to the eye or affecting the users' vision. The present invention fulfills these needs for a new form of UV radiation protection and provides other related advantages.

SUMMARY OF THE INVENTION

Advances in our understanding of the sun protective effects of organic and inorganic ingredients has lead to the development of sunscreen preparations with very effective protection against the ultraviolet rays of the sun. Until now, the effects of these ingredients has only been described for the skin, and the prior art has warned against the use of such ingredients on the ocular surface. In fact, people are asked to rinse their eyes thoroughly in case such ingredients get into their eyes. The present invention describes the specific use of such ingredients onto the ocular surface itself. The present invention proposes formulations that provide very high SPF for the eyes, while causing minimal irritation without making vision blurry.

Examples of embodiments of the present invention include compositions that are manufactured as ophthalmic solutions, emollients, creams, or ointments that can be instilled directly on the eyes. It is understood that the use of the term "ophthalmic solution" shall include emollients, creams and ointments that can be instilled directly on the eyes.

An embodiment of the present invention includes an ophthalmic solution comprised of diluted forms of an inorganic active ingredient such as titanium dioxide, zinc oxide, iron oxide, zirconium oxide, cerium oxide, or mixtures thereof. This composition may also contain a weak concentration of an organic active ingredient such as avobenzone, octinoxate, octisalate, homosalate, octocrylene, para-aminobenzoic acid, cinoxate, dioxybenzone, methyl anthranilate, octocrylene, padimate O, ensulizole, sulisobenzone, trolamine salicylate, ecamsule, and mixtures thereof.

An example embodiment of the present invention includes an ophthalmic sunscreen composition which is comprised of anywhere from 0.25% to up to 15% zinc oxide by weight.

Another example of this invention includes embodiments comprised of octinoxate and/or octisalate.

Another example of this invention includes embodiments comprised of an emulsifier, silicone- or acrylic-based, glycosides, polyethylene glycols, or a mixture thereof.

Another example of this invention includes embodiments comprised of sunscreen composition comprising an emulsifier selected from the group consisting of Arlacel P 135, DC 9011 silicone elastomer, Abil WE 09, Abil EM-90, Emulgade 68/50, Simulgel A, Simulgel EG, and mixtures thereof.

Another example of this invention includes embodiments comprised of an emollient. Said emollient may be selected from the group consisting of Aloe extracts, ethers, oleaginous esters, and mixtures thereof.

Another example of this invention includes embodiments comprised of an emollient selected from the group consisting of actiphyte of aloe vera, Cetiol OE, Lexol IPL, octyl palmitate, neopentyl glycol heptanoate, neopentyl glycol diheptanoate, Trivent NP-13, CJ2- is alkyl benzoate, and mixtures thereof.

Other features and advantages of the present invention will become apparent from the following more detailed description, when taken in conjunction with the accompanying drawings, which illustrate, by way of example, the principles of the invention.

DETAILED DESCRIPTION OF THE PREFERRED EMBODIMENTS

Examples of ophthalmic sunscreen compositions of the present invention provide an SPF of up to 50 or higher. As the eyes are usually not in direct exposure to UV radiation as opposed to the skin, such high SPF ratings may not be necessary for the present invention, and as such, the concentration of the active (and inactive) ingredients may be much lower than those proposed for dermal use.

The application of much lower concentrations of these ingredients will lead to much lower incidences of ophthalmic irritation/stinging when applied, and will lessen the known side-effects of such ingredients. Further, by reducing the concentrations of these ingredients, possible absorption of these ingredients into the eye (i.e., through the Cornea) will be reduced as to prevent possible intra-ocular effects (e.g., cataract formation).

Compositions of the present invention are now described, but are not limited to these embodiments.

Ophthalmic sunscreen compositions according to the present invention may contain a liquid vehicle base, such as an artificial tear formulation, which may be water and/or oil-based, or an ophthalmic suspension or ointment and include at least one inorganic and at least one organic active ingredient.

Inorganic active ingredients may include, but not be limited to zinc oxide, titanium dioxide, iron oxide, zirconium oxide, and cerium oxide, optionally in micronized form as to prevent blurred vision when applied.

Organic active ingredients may include, but not be limited to dioxybenzone, octinoxate, octisalate, homosalate, avobenzone, octocrylene, para-aminobenzoic acid, cinoxate, methyl anthranilate, octocrylene, padimate O, ensulizole, sulisobenzone, trolamine salicylate, and ecamsule.

The inactive ingredients of the present invention shall also include emulsifier(s) and/or emollient(s). Silicone-based emulsifiers like polyethylene glycols, polysiloxanes, glycosides are excellent choices. Acrylic-based emulsifiers, and mixtures thereof may also be used safely for the present preparation. Emollients may include, but not be limited to aloe extracts, oleaginous esters, and ethers, or a combination thereof.

The composition of the present invention shall also include, but not be limited to preservatives, chelating agents, and/or antioxidants.

The following examples describe a composition of the present invention, but it is obviously not intended to limit the scope of the invention.

Example 1

An ophthalmic sunscreen solution can be synthesized by mixing 5% micronized zinc oxide and 3% octinoxate in an ophthalmic artificial tear formulation. This solution may contain carboxymethylcellulose sodium 0.1%; glycerin 0.25%; boric acid; calcium chloride dihydrate; erythritol; levocarnitine; magnesium chloride hexahydrate; potassium chloride; purified water; sodium borate decahydrate; and sodium citrate dihydrate.

Example 2

An ophthalmic sunscreen solution can be synthesized by mixing a range of 5% micronized titanium dioxide and 3% octisalate in an ophthalmic artificial tear solution.

Example 3

An ophthalmic sunscreen ointment can be synthesized by mixing a range of 5% micronized zinc oxide and 3% octinoxate in an ophthalmic ointment consisting of hypromellose SEP, boric acid, sodium perborate, phosphonic acid, potassium chloride, purified water, and sodium chloride.

Although several embodiments have been described in detail for purposes of illustration, various modifications may be made to each without departing from the scope and spirit of the invention. Accordingly, the invention is not to be limited, except as by the appended claims.

What is claimed is:

1. A method of protecting a subject's eyes from sunlight, comprising:
   applying an ophthalmic sunscreen solution directly onto the ocular surface of the subject's eyes, wherein the ophthalmic sunscreen solution consists of an active sunscreen component and an inactive liquid vehicle base wherein the active sunscreen component consists of:
0.25 percent to 15 percent by weight of an inorganic active ingredient, selected from the group consisting of titanium dioxide, zinc oxide, iron oxide, zirconium oxide, cerium oxide and mixtures thereof; and
0.25 percent to 15 percent by weight of an organic active ingredient, selected from the group consisting of dioxybenzone, octisalate, homosalate, avobenzone, octocrylene, para-aminobenzoic acid, cinoxate, methyl anthranilate, 2-ethylhexyl 4-(dimethylamino)benzoate, ensulizole, sulisobenzone, trolamine salicylate and ecamsule; and
wherein the inactive liquid vehicle base is an ophthalmic artificial tear formulation.

2. The method of claim 1, wherein the inactive liquid vehicle base comprises an emulsifier.

3. The method of claim 2, wherein the emulsifier is selected from the group consisting of a silicone-based emulsifier, a polyethylene glycol emulsifier, a polysiloxane emulsifier, a glyscoside emulsifier, an acrylic-based emulsifier and combinations thereof.

4. The method of claim 1, wherein the inactive liquid vehicle base comprises an emollient.

5. The method of claim 4, wherein the emollient is selected from the group consisting of aloe extracts, oleaginous esters, ethers and combinations thereof.

6. The method of claim 1, wherein the inactive liquid vehicle base comprises a chelating agent.

7. The method of claim 1, wherein the inactive liquid vehicle base comprises a preservative, a chelating agent, an antioxidant, an ophthalmic lubricant, an ophthalmic astringent or ecamsule.

8. The method of claim 1, wherein the ophthalmic sunscreen solution is in the form of an eye drop, a suspension, an emulsion, or an ointment.

* * * * *